United States Patent
Graves et al.

(10) Patent No.: US 10,247,736 B2
(45) Date of Patent: Apr. 2, 2019

(54) IDENTIFICATION AND QUANTIFICATION OF BIOMARKERS FOR EVALUATING THE RISK OF PRETERM BIRTH

(75) Inventors: Steven William Graves, Highland, UT (US); Michael Sean Esplin, Salt Lake City, UT (US); Craig Dan Thulin, Lindon, UT (US)

(73) Assignees: BRIGHAM YOUNG UNIVERSITY, Provo, UT (US); UNIVERSITY OF UTAH RESEARCH FOUNDATION, Salt Lake City, UT (US); IHC HEALTH SERVICES, Salt Lake City, UT (US)

(*) Notice: Subject to any disclaimer, the term of this patent is extended or adjusted under 35 U.S.C. 154(b) by 746 days.

(21) Appl. No.: 12/669,343

(22) PCT Filed: Jul. 17, 2008

(86) PCT No.: PCT/US2008/070320
§ 371 (c)(1),
(2), (4) Date: Jul. 12, 2010

(87) PCT Pub. No.: WO2009/014987
PCT Pub. Date: Jan. 29, 2009

(65) Prior Publication Data
US 2010/0297679 A1 Nov. 25, 2010

Related U.S. Application Data

(60) Provisional application No. 60/961,466, filed on Jul. 20, 2007, provisional application No. 61/049,676, filed on May 1, 2008.

(51) Int. Cl.
G01N 33/68 (2006.01)

(52) U.S. Cl.
CPC ......... *G01N 33/6893* (2013.01); *G01N 33/68* (2013.01); *G01N 2333/811* (2013.01); *G01N 2800/368* (2013.01)

(58) Field of Classification Search
USPC ..... 435/7.1, 7.8, 7.92, 7.93, 7.94, 7.95, 331, 435/975; 436/501, 510, 518, 536, 548, 436/65, 86, 87, 814, 815; 530/324, 326, 530/380, 387.9, 388.25, 389.3, 391.1
See application file for complete search history.

(56) References Cited

U.S. PATENT DOCUMENTS

| | | | |
|---|---|---|---|
| 6,329,209 B1* | 12/2001 | Wagner | B82Y 5/00 427/261 |
| 7,091,316 B2 | 8/2006 | Uchida et al. | |
| 7,191,068 B2 | 3/2007 | Rosenfeld et al. | |
| 7,605,003 B2* | 10/2009 | Chan | G01N 33/57449 435/4 |
| 7,632,685 B2* | 12/2009 | Ivey | C12Q 1/6883 436/173 |
| 2004/0197930 A1 | 10/2004 | Rosenfeld et al. | |
| 2005/0059013 A1 | 3/2005 | Chan et al. | |
| 2005/0095611 A1* | 5/2005 | Chan | C12Q 1/6886 435/6.12 |
| 2006/0127962 A1 | 6/2006 | Buhimschi et al. | |
| 2006/0166280 A1 | 7/2006 | Strauss et al. | |
| 2007/0054329 A1 | 3/2007 | Fung et al. | |
| 2007/0178605 A1 | 8/2007 | Mor et al. | |
| 2008/0090759 A1 | 4/2008 | Kokenyesi et al. | |
| 2008/0274481 A1 | 11/2008 | Fung et al. | |
| 2010/0137263 A1* | 6/2010 | Smith | 514/169 |
| 2013/0236977 A1* | 9/2013 | Steen | G01N 33/6851 436/86 |

FOREIGN PATENT DOCUMENTS

| | | | |
|---|---|---|---|
| EP | 1914548 | 4/2008 | |
| EP | 1914552 | 4/2008 | |
| EP | 1914553 | 4/2008 | |
| WO | 1993009438 | 5/1993 | |
| WO | 2006/026557 | * 3/2006 | |
| WO | 2007022248 | 2/2007 | |
| WO | WO-2008021290 A2 * | 2/2008 | ......... G01N 33/6845 |
| WO | 2008046160 | 4/2008 | |
| WO | 2008/079407 | * 7/2008 | |
| WO | 2009014987 | 1/2009 | |

OTHER PUBLICATIONS

Cairoli et al., 2006. Serum protein pattern during cow pregnancy: acute-phase proteins increase in the peripartum period. Electrophoresis 27: 1617-1625.*
Choi-Miura, 2001. Quantitative measurement of the novel human plasm protein, IHRP, by sandwich ELISA. Biol. Pharm. Bull. 24: 214-217.*
Goldenberg et al., 2005. Biochemical markers for the prediction of preterm birth. Am J. Obstet. Gynecol. 192: S36-S46.*
Pereira et al., 2006. Peptide profiling of maternal serum to detect spontaneous preterm birth and intra-amniotic infection among women in preterm labor. Am. J. Obstet. Gynecol. 195 (6 Suppl.): S10.*
Salier et al., 1996. The inter-alpha-inhibitor family: from structure to regulation. Biochemical Journal 315: 1-9.*
Merrell et al. "Analysis of Low-Abundance, Low-Molecular-Weight Serum Proteins Using Mass Spectrometry" J Biomol Tech. Dec. 2004;15(4):238-48 (Year: 2004).*
Harlow et al. "Antibodies: A Laboratory Manual" (1988) Cold Spring Harbor Laboratory Press, Cold Spring Harbor, NY, pp. 23-24 and 72-76 (Year: 1988).*
Wolfe, S.L., Molecular and Cellular Biology, 1993, pp. 790-793 (Year: 1993).*

(Continued)

*Primary Examiner* — Christine Foster
(74) *Attorney, Agent, or Firm* — Brooks Kushman P.C.

(57) ABSTRACT

Described herein are methods for evaluating the risk of preterm birth in pregnant subjects. The methods involve detecting and quantifying one or more biomarkers associated with preterm birth in a biological sample from the subject. Also described herein are isolated biomarkers and kits useful in predicting the risk of preterm birth.

16 Claims, No Drawings
Specification includes a Sequence Listing.

(56) References Cited

OTHER PUBLICATIONS

Kuby et al. Immunology, W.H. Freeman and Company (1992), p. 125 (Year: 1992).*
Bost et al. Immunol. Invest. 1988; 17:577-586 (Year: 1988).*
Bendayan J. Histochem. Cytochem. 1995; 43:881-886 (Year: 1995).*
Polson et al. "Optimization of protein precipitation based upon effectiveness of protein removal and ionization effect in liquid chromatography—tandem mass spectrometry" Journal of Chromatography B, 785 (2003) 263-275 (Year: 2003).*
Ma et al. "A fully automated plasma protein precipitation sample preparation method for LC—MS/MS bioanalysis" Journal of Chromatography B, 862 (2008) 219-226, Available online Dec. 24, 2007 (Year: 2007).*
International Search Report dated Oct. 26, 2010 for international application No. PCT/US10/45957.
Menon et al. "Genetic regulation of amniotic fluid TNF-alpha and soluble TNF receptor concentrations affected by race and preterm birth." Human Genet., Oct. 2008; vol. 124, No. 3; p. 243, only.
Scholl et al. "Anemia, Iron and Pregnancy Outcome." Feb. 2000; vol. 130; Suppl 2S; pp. 443S-447S.
Catov et al. "Activation of the Fibrinolytic Cascade Early in Pregnancy Among Women With Spontaneous Preterm Birth. Obstet Gynecol.", Nov. 2008; vol. 112, No. 5; pp. 1116-1122.
Goldenberg et al. "The preterm prediction study: cervical lactoferrin concentration, other markers of lower genital tract infection, and preter, birth." National Institute of Child Health and Human Development Maternal-Fetal Medicine Units Network. Am J Obstet Gynecol., Mar. 2000; vol. 182, No # pp. 631-635.
Hobel et al. Maternal plasma corticotropin-releasing hormone associated with stress at 20 weeks gestation in pregnancies ending in preterm delivery. Am J Obstet Gynecol., Jan. 1999; vol. 180, No. 1, Pt 3; pp. S257-S2263.
International Search Report dated Jan. 12, 2009 for international application No. PCT/US08/70320.
European Search Report dated Jun. 18, 2010 for European application No. EP08796232.0-2404.
Song Jin et al. "Quantification of fragments of human serum inter-alpha-trypsin inhibitor heavy chain 4 by a surface-enhanced laser desorption/ionization-based immunoassay" Clinical Chemisrty, vol. 52, No. 6, Jun. 2006, pp. 1045-1053.
Heitner J C et al. "Differentiation of HELLP patients from healthy pregnant women by proteome ananlysis—On the way towards a clinical marker set" Journal of Chromatography B: Biomedical Sciences & Applications, Elsevier, Amsterdam, NL LNKD-DOI: 10.1016/J. JCHROMB.2006.06.002, vol. 840, No. 1, Aug. 2006, pp. 10-19.
Geisert R D et al. "Expression of an inter-alpha-trypsin inhibitor heavy chain-like protein in the pig endometrium during the oestrous cycle and early pregnancy" Journal of Reproduction and Fertility, Endocrinology, Dehli, vol. 114, No. 1, Sep. 1998, pp. 35-43.
Response to European Search Report dated Jan. 14, 2011.

* cited by examiner

SEQUENCE LISTING

```
<160> NUMBER OF SEQ ID NOS: 4

<210> SEQ ID NO 1
<211> LENGTH: 19
<212> TYPE: PRT
<213> ORGANISM: Homo sapiens

<400> SEQUENCE: 1

Gln Leu Gly Leu Pro Gly Pro Pro Asp Val Pro Asp His Ala Ala Tyr
1               5                   10                  15

His Pro Phe

<210> SEQ ID NO 2
<211> LENGTH: 41
<212> TYPE: PRT
<213> ORGANISM: Homo sapiens

<400> SEQUENCE: 2

Asn Val His Ser Ala Gly Ala Ala Gly Ser Arg Met Asn Phe Arg Pro
1               5                   10                  15

Gly Val Leu Ser Ser Arg Gln Leu Gly Leu Pro Gly Pro Pro Asp Val
            20                  25                  30

Pro Asp His Ala Ala Tyr His Pro Phe
        35                  40

<210> SEQ ID NO 3
<211> LENGTH: 41
<212> TYPE: PRT
<213> ORGANISM: Homo sapiens
<220> FEATURE:
<221> NAME/KEY: MISC_FEATURE
<222> LOCATION: (12)..(12)
<223> OTHER INFORMATION: Xaa at residue 12 represents oxidized
      methionine. Throughout the application it is referred to as M(O).

<400> SEQUENCE: 3

Asn Val His Ser Ala Gly Ala Ala Gly Ser Arg Xaa Asn Phe Arg Pro
1               5                   10                  15

Gly Val Leu Ser Ser Arg Gln Leu Gly Leu Pro Gly Pro Pro Asp Val
            20                  25                  30

Pro Asp His Ala Ala Tyr His Pro Phe
        35                  40

<210> SEQ ID NO 4
<211> LENGTH: 28
<212> TYPE: PRT
```

```
<213> ORGANISM: Homo sapiens

<400> SEQUENCE: 4

Asn Val His Ser Gly Ser Thr Phe Phe Lys Tyr Tyr Leu Gln Gly Ala
1               5                   10                  15

Lys Ile Pro Lys Pro Glu Ala Ser Phe Ser Pro Arg
            20                  25
```

IDENTIFICATION AND QUANTIFICATION OF BIOMARKERS FOR EVALUATING THE RISK OF PRETERM BIRTH

CROSS REFERENCE TO RELATED APPLICATIONS

This application is the U.S. national phase of PCT Application No. PCT/US2008/070320 filed on Jul. 17, 2008, which claims priority upon U.S. provisional application Ser. No. 60/961,466 filed Jul. 20, 2007 and U.S. provisional application Ser. No. 61/049,676 filed May 1, 2008. These applications are hereby incorporated by reference in their entireties for all of their teachings.

ACKNOWLEDGEMENTS

The research leading to this invention was funded in part by the National Institutes of Health, Grant Nos. R21HD047319 and U01HD050080. The U.S. Government has certain rights in this invention.

CROSS REFERENCE TO SEQUENCE LISTING

Amino acid sequences described herein are referred to by a sequence identifier number (SEQ ID NO). The SEQ ID NO corresponds numerically to the sequence identifiers <400>1, <400>2, etc. The Sequence Listing, in written computer readable format (CFR), is incorporated by reference in its entirety.

SEQUENCE LISTING

The text file Sequences_003_ST25.txt of size 2 KB created 18 Dec. 2017, filed herewith, is hereby incorporated by reference.

BACKGROUND

Preterm delivery affects more than 10% of all pregnant mothers. It is also one of the leading causes of illness and death associated with newborns. Compared with babies born at term, infants born prematurely experience a 40-fold increase in neonatal death, and may be at significantly increased risk for major medical complications such as cerebral palsy, chronic respiratory illness, blindness and deafness. Furthermore, long-term neurologic and developmental problems have been identified in as many as 70% of children with birth weight less than 1.5 lbs. It has been estimated that these complications are associated with billions of dollars of direct costs and unrealized potential each year just in the United States.

Despite the significance of the problem, there has been uncertainty as to what occurs in the body that leads to preterm labor and delivery. Although the ability to effectively treat these problems remain limited due to the uncertainty that exists regarding the causes of preterm birth (PTB), medical measures may be taken by medical professionals if given adequate advance warning. If one could predict which pregnant mothers were likely to experience preterm birth, medications may be administered that might delay or even prevent premature delivery. Additionally, there hormone derivatives are known that can enhance fetal lung maturity and thus reduce one of the major complications associated with preterm birth if administered to the fetus via the mother if the risk of preterm birth is detected sooner than later. However, at present there appears to be no way of knowing which pregnant mothers are at risk to develop this complication of pregnancy. Therefore, an important unmet need is to formulate a testing procedure for the early detection of mothers at risk for preterm birth.

SUMMARY

Described herein are methods for evaluating the risk of preterm birth in pregnant subjects. The methods involve detecting and quantifying one or more biomarkers associated with preterm birth in a biological sample from the subject. The biomarkers useful in predicting preterm birth are also described in detail. The advantages of the invention will be set forth in part in the description which follows, and in part will be obvious from the description, or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

DETAILED DESCRIPTION

Before the present compounds, compositions, and/or methods are disclosed and described, it is to be understood that the aspects described below are not limited to specific compounds, synthetic methods, or uses as such may, of course, vary. It is also to be understood that the terminology used herein is for the purpose of describing particular aspects only and is not intended to be limiting.

In this specification and in the claims that follow, reference will be made to a number of terms that shall be defined to have the following meanings:

It must be noted that, as used in the specification and the appended claims, the singular forms "a," "an" and "the" include plural referents unless the context clearly dictates otherwise. Thus, for example, reference to "a biomarker" includes mixtures of two or more such biomarkers, and the like.

"Optional" or "optionally" means that the subsequently described event or circumstance can or cannot occur, and that the description includes instances where the event or circumstance occurs and instances where it does not.

As used herein, "subject" refers to a pregnant woman at risk for preterm birth and benefits from the methods described herein.

As used herein "preterm birth" includes the delivery of a baby prior to full gestation. For example, delivery of the baby less than 37 weeks of gestation is considered a preterm birth. The term preterm birth is synonymous with preterm delivery and premature delivery.

As used herein, the term "biomarker" may be used to refer to a naturally-occurring biological molecule present in pregnant women at varying concentrations useful in predicting the risk of preterm birth. For example, the biomarker can be a peptide present in higher or lower amounts in a subject at risk of preterm birth relative to the amount of the same biomarker in a subject who did not experience preterm birth. The biomarker can include other molecules besides peptides including small molecules such as but not limited to biological amines and steroids.

As used herein, the term "peptide" may be used to refer to a natural or synthetic molecule comprising two or more amino acids linked by the carboxyl group of one amino acid to the alpha amino group of another. The peptide is not limited by length, and thus "peptide" can include polypeptides and proteins.

As used herein, the term "isolated," with respect to peptides, refers to material that has been removed from its original environment, if the material is naturally occurring. For example, a naturally-occurring peptide present in a living animal is not isolated, but the same peptide, which is separated from some or all of the coexisting materials in the natural system, is isolated. Such isolated peptide could be part of a composition and still be isolated in that the composition is not part of its natural environment. An "isolated" peptide also includes material that is synthesized or produced by recombinant DNA technology.

As use herein, the term "specifically immunoreactive" refers to a measurable and reproducible specific immunoreaction such as binding between a peptide and an antibody that is determinative of the presence of the peptide in a biological sample or in a heterogeneous population of peptides and other biologics. The term "specifically immunoreactive" may include specific recognition of structural shapes and surface features. Thus, under designated conditions, an antibody specifically immunoreactive to a particular peptide does not bind in a significant amount to other peptides present in the sample. A variety of immunoassay formats can be used to determine antibodies specifically immunoreactive to a particular peptide. For example, solid-phase ELISA immunoassays are routinely used to select monoclonal antibodies specifically immunoreactive with a peptide. See, e.g., Harlow and Lane (1988) Antibodies, A Laboratory Manual, Cold Spring Harbor Publications, New York, which is incorporated herein by reference, for a description of immunoassay formats and conditions that can be used to determine specific immunoreactivity.

As used herein, the term "antibody" refers to an immunoglobulin specifically immunoreactive to a given antigen. The term "antibody" is intended to include whole antibodies of any isotype (IgG, IgA, IgM, IgE, etc), and fragments thereof. An "antibody" as sued herein also includes an antibody preparation. Antibodies may be labeled with detectable labels using a variety of techniques as is known in the art. The label can be a radioisotope, fluorescent compound, chemiluminescent compound, enzyme, or enzyme co-factor, or any other labels known in the art. In some aspects, the antibody that binds to the peptide of interest may not be labeled, but may instead be detected by binding of a labeled secondary antibody that specifically binds to the primary antibody.

As used herein, the term "detect" refers to the quantitative measurement of undetectable, low, normal, or high serum concentrations of one or more biomarkers such as, for example, peptides and other biological molecules.

As used herein, the terms "quantify" and "quantification" may be used interchangeably, and refer to a process of determining the quantity or abundance of a substance in a sample (e.g., a biomarker), whether relative or absolute.

As used herein, the term "about" is used to provide flexibility to a numerical range endpoint by providing that a given value may be "a little above" or "a little below" the endpoint without affecting the desired result.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 1 to about 5" should be interpreted to include not only the explicitly recited values of about 1 to about 5, but also include individual values and sub-ranges within the indicated range. Thus, included in this numerical range are individual values such as 2, 3, and 4 and sub-ranges such as from 1-3, from 2-4, and from 3-5, etc., as well as 1, 2, 3, 4, and 5, individually. This same principle applies to ranges reciting only one numerical value as a minimum or a maximum. Furthermore, such an interpretation should apply regardless of the breadth of the range or the characteristics being described.

Described herein are methods for identifying pregnant subjects that are at risk for preterm birth. Particular biomarkers have been identified that may be utilized to identify pregnant subjects during early to mid-pregnancy that may be at risk for preterm birth. Such markers may allow the diagnostic distinction between preterm birth and other conditions that exhibit similar symptoms. Early identification of subjects at greater risk for preterm birth would be of considerable value, as such subjects could be more closely monitored.

Testing of pregnant subjects using the methods described herein may occur at any time during pregnancy when biomarkers indicative of preterm birth are quantifiable in the subject. For example, in one aspect biomarkers may be tested at from about 20 weeks to about 34 weeks gestation. In another aspect, biomarkers may be tested at from about 24 weeks to about 32 weeks gestation. It should be noted that these ranges should not be seen as limiting, as such testing may be performed at any point during pregnancy. Rather these ranges are provided to demonstrate periods of the gestational cycle where such testing is most likely to occur in a majority of subjects.

Useful biomarkers in identifying subjects at risk for preterm birth include various peptides and other biological molecules. Certain peptides and other biological molecules have been identified using the techniques and methods described herein that correlate with the incidence of preterm birth. Quantification of one or more of these peptides and other biological molecules provides some indication of the risk of preterm birth for the subject, and thus may provide opportunities for preventative treatments. It should be noted that any biomarker that is predictive of preterm birth complications should be considered to be within the scope of the claims of the present invention. In one aspect, however, nonlimiting examples of biomarkers associated with preterm birth complications may include biological molecules and peptides found to be statistically different ($p \leq 0.01$) from control subjects (i.e., pregnant women that did not experience preterm birth complications), and a p (probability) value<0.02 served as the cutoff. In another aspect, however, nonlimiting examples of peptides associated with preterm birth may include peptides having amino acid sequences of QLGLPGPPDVPDHAAYHPF (SEQ ID NO 1), NVHSA-GAAGSRMNFRPGVLSSRQLGLPGPPDVPDHAAYHPF (SEQ ID NO 2), NVHSAGAAGSRM$^{(O)}$NFRPGVLSS- RQLGLPGPPDVPDHAAYHPF (SEQ ID NO 3), where M$^{(O)}$ represents an oxidized methionine, and NVHSGSTFFKYYLQGAKIPKPEASFSPR (SEQ ID NO 4).

The proteomic techniques used to identify biomarkers as disclosed in International Publication No. WO 2008/079407, which is hereby incorporated by reference in their entirety for all purposes within this application, can be used to identify and quantify biomarkers for evaluating the risk of preterm birth in a pregnant subject. In one aspect, a method for testing a pregnant subject for potential preterm birth may include detecting the difference in concentration or amount of one or more biomarkers associated with preterm birth present in a biological sample compared to a control (i.e., the relative concentration or amount of the biomarker(s) in a pregnant woman that does not experience preterm birth). In one aspect, proteomic systems and methods can be used to identify and quantify the biomarkers. For example, comparing multiple mass spectra from different biological samples, locating mass ions that are quantitatively different after using approaches to compensate for non-biological variability, isolating, and characterizing the biomarker of interest can be used herein. Such a method may include fractionating each of a plurality of biological samples to form a plurality of elutions, obtaining a plurality of mass spectra from each of the plurality of elutions at a plurality of elution times, and finding a molecular ion peak of interest that appears to be quantitatively different between biological samples. The method may additionally include identifying a mass spectrum reference peak corresponding to an endogenous reference molecule that is substantially consistent between biological samples, the endogenous reference molecule having an elution time and a mass to charge ratio that are substantially similar to the peak of interest, and compensating for non-biological variation for each biological sample across the plurality of elutions by normalizing the peak of interest to a mass spectrum peak of the endogenous reference molecule. The method may further include conducting collision-induced fragmentation studies that use each of a plurality of collision energies one run at a time and summing resulting pluralities of fragment ion mass spectra without averaging to form a single cumulative daughter fragment mass spectrum, and use the daughter fragment mass spectrum to establish amino acid sequence data which is then used in identifying a peptide corresponding to a peak of interest in the single aligned mass spectrum.

In another aspect, a biological sample containing the biomarker(s) of interest can be fractionated to form a plurality of elutions, obtaining a plurality of mass spectra from each of the plurality of elutions at a plurality of elution times, and identifying a mass spectrum alignment peak corresponding to an endogenous alignment molecule that elutes in each of the plurality of elutions. The method may further include aligning the pluralities of mass spectra from each elution by aligning the mass spectrum alignment peak from each of the plurality of elutions, summing the pluralities of aligned mass spectra to form a single aligned mass spectrum, and identifying a peptide corresponding to a peak of interest in the single aligned mass spectrum. Although various techniques are contemplated, in one aspect aligning the pluralities of mass spectra may further include visually aligning the pluralities of mass spectra. Additionally, fractionating each of the plurality of biological molecules present in a plurality of biological samples may be accomplished by numerous methods, for example by capillary liquid chromatography (cLC). Specific methods and parameters for detecting and quantifying the biomarkers described herein are provided in the Examples.

The proteomic techniques used to detect and quantify the biomarkers make use of molecules native to all sera that serve as internal controls that can be used to correct for differences in specimen loading, ionization efficiency and mass spectrometer sensitivity. Further to above discussion, a peak is chosen as a reference if it can be shown to be quantitatively similar between comparison groups, elutes from the column in the same elution window as the candidate biomarker, is similar in its mass to charge ratio to that of the candidate biomarker, and is sufficiently abundant that every specimen will have a quantity that is more than 3 times the level of noise. The reference peaks described here are for quantitative correction of peak height or area that is related to specimen processing, chromatographic loading, ionization efficiency or instrumental sensitivity fluctuations but not due to biologic differences in peak quantity. This reference is termed an internal quantitative control. In other aspects, external controls can be used to facilitate the quantification of the biomarker. In this aspect, a compound in a known amount can be added to the biological sample so that a ratio of biomarker to control can be calculated. The ratio can then be compared to ratios from control samples in order to assess the risk of preterm birth.

As described above, four biomarkers (SEQ ID NOS 1-4) have been identified as predictors of preterm birth. Internal quantitative controls were used to quantify the biomarkers. The reference (i.e., internal control) used for the biomarker SEQ ID NO 1 (m/z 677) had an m/z of 673.36 for its +3 charge state for the monoisotopic peak. The neutral parent mass was 2017.07 mass units, and the chromatographic elution time was 15.5 min. However, given that elution time will vary somewhat on different days or with replacement columns, the elution time is provided as a fraction of its elution time relative to the internal time control (0.9968, i.e. it elutes 0.0032 times its own retention time earlier than the internal time control) and as a fraction of its elution time compared with the actual biomarker SEQ ID NO 1 (m/z 677) (1.0558, i.e. it elutes 0.05286 of its own elution time sooner than the biomarker).

The second internal quantitative control served as a reference for the two biomarkers SEQ ID NO 2 (m/z 857) and SEQ ID NO 3 (m/z 860). The m/z of the reference molecule was 842.39 in its +5 charge state with a neutral parent mass of 4206.07 mass units. The chromatographic elution time was approximately 15.8 min. However, given elution time variability its elution time is more appropriately described in relation to the elution times of the internal time control and the biomarker SEQ ID NO 2 (m/z 857). In relation to the internal time control, the internal quantitative control eluted a factor of 0.0159 times the elution time its own elution time after the elution of the internal time control (or a ratio of 1.0161 of the time control marker). In relation to the SEQ ID NO 2 (m/z 857) biomarker, the internal quantitative marker came off by a factor of 0.0539 times its own elution time after the biomarker (or a factor of 1.0700 of the elution time of the biomarker).

The reference used for the biomarker SEQ ID NO 4 (m/z 795) had an m/z of 595.3 for its +1 charge state for the monoisotopic peak. The neutral parent mass was 594.32 mass units, and the chromatographic elution time was 18.8 min However, given that elution time will vary somewhat on different days or with replacement columns, the elution time is provided as a fraction of its elution time relative to the two internal time controls, the one that precedes it (1435.2) and the one that follows it (2009.95), i.e. it elutes 0.607 of the way through that interval specified by the two boundary time alignment markers.

Although individual masses may be defined by elution time (retention time), elution time (retention time) can also be expressed as a function of internal time controls. This is determined by the relative position of the peak of interest between the time maker that precedes the biomarker and the time marker that follows the peak of interest. This determination is deemed an $R_f$ value. $R_f$ values are calculated as follows:

$R_f$=(elution time of biomarker−elution time of preceding time marker)/(elution time of following time marker−elution time of preceding time marker).

Using the techniques described above, four biomarkers have been identified as indicators for preterm birth. Specific details regarding the identification and quantification of the biomarkers is provided in the Examples. Additional structural properties of each biomarker are provided below. The first biomarker ("SEQ ID NO 1"), which is a peptide, has a mass ion peak (m/z) at 677, a mean mass of 2026.98 Daltons, a mean elution time of 14.30±0.47 minutes, and a $R_f$ value of 0.535±0.052. SEQ ID NO 1 is also referred to herein as "biomarker 1."

The second biomarker (SEQ ID NO 2), which is a peptide, has a mass ion peak (m/z) at 857, a mean mass of 4279.25 Daltons, a mean elution time of 17.20±2.04 minutes, and a $R_f$ value of 0.781±0.086. SEQ ID NO 2 is also referred to herein as "biomarker 2."

The third biomarker (SEQ ID NO 3), which is a peptide, has a mass ion peak (m/z) at 860, a mean mass of 4295.25 Daltons, a mean elution time of 16.13±1.97 minutes, and a $R_f$ value of 0.695±0.134. SEQ ID NO 3 is also referred to herein as "biomarker 3."

The fourth biomarker (SEQ ID NO 4), which is a peptide, has a mass ion peak (m/z) at 795, a mean mass of 3968.96 Daltons, a mean elution time of 15.52±0.15 minutes, and a $R_f$ value of 0.0252±0.021. SEQ ID NO 4 is also referred to herein as "biomarker 4."

Accordingly, a method for evaluating a pregnant subject for potential preterm birth is provided. In one aspect, the method includes detecting at least one biomarker described herein associated with a preterm birth in a biological sample from the subject, where the at least one biomarker has an amino acid sequence that is identical with or homologous to a sequence, a sequence represented by SEQ ID NO 1, SEQ ID NO 2, SEQ ID NO 3, or SEQ ID NO 4 and quantifying an abundance of the at least one biomarker in the biological sample. The abundance of the biomarker is measured following processing and separation as a function of a reference molecule also present in the biological sample that serves as an internal control. The term "abundance" as used herein represents the number of ions of a particular mass measured by the mass spectrometer in a given mass spectrum or the sum of the number of ions of a specific mass observed in several mass spectra representing the full elution interval. Normalization of biomarker abundance to this internal control reduces non-biological variation and improves the ability to utilize biomarkers in risk prediction. Stated another way, by choosing a molecule for a reference that is present in a biological sample in an abundance that is relatively constant from one subject to another, variability in the processing of biological samples can be corrected for, particularly when comparing runs conducted on different days that may be spread out over long periods of time. As such, the relative abundance of a biomarker may vary depending on the particular biomarker involved. A particular cutoff value may therefore be established for each biomarker/reference ratio such that ratios of the biomarker peak abundance to the reference peak abundance above or below a certain value may be predictive of a substantially increased risk of preterm birth.

Testing for potential preterm birth may also be accomplished by comparing the abundance of one or more biomarkers in a biological sample from a subject with a known abundance of those same biomarkers that is indicative of a normal birth. In one aspect, preterm birth may occur if a subject has a measured abundance of SEQ ID NO 1 that is less than about 50% of the abundance of the control at least 22 weeks gestation. In another aspect, preterm birth may occur if a subject has a measured abundance of SEQ ID NO 1 that is less than about 30% of the abundance of the control at least 22 weeks gestation. In yet another aspect, preterm birth may occur if a subject has a measured abundance of SEQ ID NO 1 that is less than about 10% of the abundance of the control at least 22 weeks gestation In another aspect, preterm birth may occur if a subject has a measured abundance of SEQ ID NO 2 that is less than about 50% of the abundance of the control at least 22 weeks gestation. In another aspect, preterm birth may occur if a subject has a measured abundance of SEQ ID NO 2 that is less than about 30% of the abundance of the control at least 22 weeks gestation. In yet another aspect, preterm birth may occur if a subject has a measured abundance of SEQ ID NO 2 that is less than about 10% of the abundance of the control at least 22 weeks gestation.

In a further aspect, preterm birth may occur if a subject has a measured abundance of SEQ ID NO 3 that is less than about 55% of the abundance of the control at least 22 weeks gestation. In another aspect, preterm birth may be suggested if a subject has a measured abundance of SEQ ID NO 3 that is less than about 35% of the abundance of the control at least 22 weeks gestation. In yet another aspect, preterm birth may occur if a subject has a measured abundance of SEQ ID NO 3 that is less than about 15% of the abundance of the control at least 22 weeks gestation.

In yet another aspect, preterm birth may occur if a subject has a measured abundance of SEQ ID NO 4 that is less than about 50% of the abundance of the control at least 22 weeks gestation. In another aspect, preterm birth may be suggested if a subject has a measured abundance of SEQ ID NO 4 that is less than about 30% of the abundance of the control at least 22 weeks gestation. In yet another aspect, preterm birth may occur if a subject has a measured abundance of SEQ ID NO 4 that is less than about 10% of the abundance of the control at least 22 weeks gestation.

Any type of biological sample that may contain a biomarker of interest may be screened, including such non-limiting examples as serum, plasma, blood, urine, cerebrospinal fluid, amniotic fluid, synovial fluid, cervical vaginal fluid, lavage fluid, tissue, and combinations thereof.

Although biomarkers 1-4 are present in most pregnant women, many pregnant women that go on to experience preterm birth had lower blood serum concentrations of one or more of these biological molecules during pregnancy as compared to women that had normal births. For example, biomarkers 1-4 either alone or collectively were less abundant in PTB cases than in the controls. Thus, a comparison of the abundance of one or more of these biomarkers in a biological sample from a subject against a known control concentration from subjects that did not experience preterm birth, or against a known biomarker concentration from the subject being tested, may be predictive of preterm birth.

Those subjects having a higher or lower abundance of one or more of these biomarkers may have an increased risk of preterm birth, and can thus be identified early enough to allow appropriate treatment. The abundance of a particular biomarker in predicting preterm birth is described in detail below.

In one aspect, to calculate biomarker abundance of preterm birth subjects and control subjects, log ratios were taken. For example, the log ratio of log 676.7/673.36 (biomarker 1/reference peak) yielded a mean control of 0.579±0.101 and a mean PTB of −0.015±0.090. The log ratio of log 856.8/842.8 (biomarker 2/reference peak) yielded a mean control (subjects who did not experience preterm birth) of 0.231±0.102 and a mean PTB (subjects at risk for preterm birth) of −0.149±0.095 (Table 4 in Examples). Referring to Table 4 in the Examples, the log ratios of the other biomarkers were calculated. The log ratio of log 860.0/842.8 (biomarker 3/reference peak) yielded a mean control of 0.201±0.096 and a mean PTB of −0.204±0.088. The log ratio of log 794.8/595.3 (biomarker 4/reference peak) yielded a mean control of 0.582±0.637 and a mean PTB of 0.274±0.656. Stated another way, a subject at risk for preterm birth would most likely exhibit an decrease in biomarker 1, a decrease in biomarker 2, a decrease in biomarker 3, and a decrease in biomarker 4 either individually or collectively.

With that description in mind, in one aspect, it may be predictive of a substantially increased risk of preterm birth if the ratio of the abundance of SEQ ID NO 1 (m/z 677) to the abundance of a reference molecule at m/z 673 is measured to be less than about 1.0 at least 22 weeks gestation. In another aspect, it may be predictive of a substantially increased risk of preterm birth if the ratio of the abundance of SEQ ID NO 1 (m/z 677) to the abundance of a reference molecule at m/z 673 is measured to be less than about 0.8 at least 22 weeks gestation. In yet another aspect, it may be predictive of a substantially increased risk of preterm birth if the ratio of the abundance of SEQ ID NO 1 (m/z 677) to the abundance of a reference molecule at m/z 673 is measured to be less than about 0.6 at least 22 weeks gestation.

Furthermore, in one aspect it may be predictive of a substantially increased risk of preterm birth if the ratio of the abundance of SEQ ID NO 2 (m/z 857) to the abundance of a reference molecule at m/z 843 is measured to be less than about 0.6 at least 22 weeks gestation. In another aspect, it may be predictive of a substantially increased risk of preterm birth if the ratio of the abundance of SEQ ID NO 2 (m/z 857) to the abundance of a reference molecule at m/z 843 is measured to be less than about 0.5 at least 22 weeks gestation. In yet another aspect, it may be predictive of a substantially increased risk of preterm birth if the ratio of the abundance of SEQ ID NO 2 (m/z 857) to the abundance of a reference molecule at m/z 843 is measured to be less than about 0.44 at least 22 weeks gestation.

Additionally, in one aspect, it may be predictive of a substantially increased risk of preterm birth if the ratio of the abundance of SEQ ID NO 3 (m/z 860) to the abundance of a reference molecule at m/z 843 is measured to be less than about 0.6 at least 22 weeks gestation. In another aspect, it may be predictive of a substantially increased risk of preterm birth if the ratio of the abundance of SEQ ID NO 3 (m/z 860) to the abundance of a reference molecule at m/z 843 is measured to be less than about 0.4 at least 22 weeks gestation. In yet another aspect, it may be predictive of a substantially increased risk of preterm birth if the ratio of the abundance of SEQ ID NO 3 (m/z 860) to the abundance of a reference molecule at m/z 843 is measured to be less than about 0.2 at least 22 weeks gestation.

In a further aspect, it may be predictive of a substantially increased risk of preterm birth if the ratio of the abundance of SEQ ID 4 (m/z 795) to the abundance of reference molecule at m/z 595 is measure to be less than about 0.6 at least 22 weeks gestation. In another aspect, it may be predictive of a substantially increased risk of preterm birth if the ratio of the abundance of SEQ ID NO 4 (m/z 795) to the abundance of a reference molecule at m/z 595 is measured to be less than about 0.4 at least 22 weeks gestation. In yet another aspect, it may be predictive of a substantially increased risk of preterm birth if the ratio of the abundance of SEQ ID NO 4 (m/z 795) to the abundance of a reference molecule at m/z 595 is measured to be less than about 0.2 at least 22 weeks gestation.

In certain aspects, the log ratios calculated above may be used to statistically predict the risk of pregnant women at risk of experiencing preterm birth. One common measure of the predictive power of a biomarker is its sensitivity and specificity. "Sensitivity" as used herein is a statistical term defined as the true positive rate (e.g., the percentage of pregnant women who later experience preterm birth that are correctly identified by the biomarker). The term "specificity" as used herein is defined as the true negative rate (e.g., the percentage of pregnant women with uncomplicated pregnancies correctly identified). To use a biomarker as described herein for predicting preterm birth, a numeric threshold is established. To establish a numeric threshold, the range of values for the specific biomarker are considered from lowest to highest and at each point the percent of subjects correctly identified as positive and at that same point the percent of controls incorrectly identified as positive. The range of values for the specific biomarker may be calculated by taking the actual quantitative value from the lowest to highest for a specific data set. This is termed a receiver operator curve (ROC). In one aspect, the false positive rate can be limited to 20%, which is commonly considered the maximum value tolerated for a clinical test. The false positive rate (i.e., the percentage of women with uncomplicated pregnancies identified by the biomarker at risk for experiencing preterm birth) is calculated from the true negative rate subtracted from 100%. The threshold at a false positive rate of 20% or less, which is equivalent to a specificity of 80% or higher, determines the threshold used to determine whether someone is at risk or is not at risk.

Referring to Table 5 in the Examples, a threshold for each of the four log ratios was determined for the identification of subjects at risk for preterm birth. The threshold for each was calculated such that there would be a specificity (a true negative rate) of 80% or more, which is the same as a false positive rate of no more than 20%. Using the mathematically determined thresholds, the four ratios independently provided sensitivity (true positive) and specificity (true negative) rates (Table 5). Referring to Table 5, the ratio of biomarker 1/reference peak provided the greatest sensitivity (65%) and specificity (85%) with respect to predicting preterm birth. Thus, in this aspect, the identification and quantification of biomarker 1 present in pregnant women is an accurate predictor of the likelihood of experiencing preterm birth. Although the ratio of biomarker 1/reference peak is useful, it is also contemplated that the combination of log ratios can be used to predict the risk of preterm birth. Thus, the biomarkers identified herein are powerful tools in predicting the risk of preterm birth.

The biomarkers described herein can be predictive of preterm birth. However, in some cases the predictive value of a test for preterm birth may be improved by screening for and quantifying multiple biomarkers. In one aspect, a biological sample from a subject may be screened for at least two biomarkers having amino acid sequences that are identical with or homologous to sequences represented by SEQ ID NO 1, SEQ ID NO 2, SEQ ID NO 3, or SEQ ID NO 4. In another aspect, a biological sample from a subject may be screened for at least three biomarkers having sequences that are identical with or homologous to sequences represented by SEQ ID NO 1, SEQ ID NO 2, SEQ ID NO 3, and SEQ ID NO 4. The predictive value may also vary depending on the type of test or assay being utilized, some of which are discussed in more detail herein. By assessing the presence and amount of multiple biomarkers (i.e., two or more), it is possible to produce fingerprints useful in predicting preterm birth. For example, the determination and quantification of at least two biomarkers can increase the predictive value of the methods described herein. Although fewer women who develop PTB may be included, it is more indicative of the risk of experiencing preterm birth. Any type of biological sample that may contain a peptide of interest may be screened, including such non-limiting examples as serum, plasma, blood, urine, cerebrospinal fluid, amniotic fluid, synovial fluid, cervical vaginal fluid, lavage fluid, tissue, and combinations thereof. In one aspect, however, it may be convenient to screen for peptides in a serum sample obtained from a subject. In another aspect, it may be convenient to screen for peptides in a blood sample obtained from the subject.

Also described herein are isolated peptides (i.e., biomarkers) and mixtures of isolated peptides that may be utilized to predict the probability that a pregnant subject will experience preterm birth. Such peptides may be useful as positive controls in many testing assays, as well as for the generation of antibodies. In one aspect, for example, an isolated peptide may have an amino acid sequence that is identical with or homologous to a sequence represented by SEQ ID NO 1 SEQ ID NO 2, SEQ ID NO 3, or SEQ ID NO 4. Peptide synthesis is well known in the art, and it is understood that one of ordinary skill in the art would be capable of using a variety of techniques to synthesize the peptides disclosed herein once in possession of the peptide sequences. Such techniques may include, without limitation, liquid-phase syntheses and solid-phase synthesis methods, as well as various methods of chemical ligation, such as prior thiol capture, native chemical ligation, expressed protein ligation, acyl initiated capture, and Staudinger ligation methods to name a few. Additionally, peptides may also be synthesized using recombinant DNA technologies.

In certain aspects, the proteomics techniques described above can be used to identify and quantify the biomarkers; however, other methods capable of detecting and/or quantifying the biomarker in a biological sample according can be used herein. One potential type of peptide assay includes immunoassays. Numerous immunoassay protocols are known that utilize antibodies to screen a biological sample for specific peptides, including homogenous, and nonhomogenous, as well as competitive and noncompetitive methods. For example, such techniques may include the use of solid supports, immunoprecipitation, etc. Generally, however, immunoassays for the detection of peptides often involve using labeled antibodies. Such labels may include any type of material known, including fluorescent labels, chemiluminescent labels, radioactive labels, enzyme labels, etc. As such, it should be understood that such immunoassay testing is well known in the art, and the particular method utilized to detect peptides in the biological sample should not be seen as limiting to the scope of the claims of the present invention. Immunoassays are discussed more fully below.

In other aspects, antibodies that are specifically immunoreactive to the biomarkers described herein can be used. In one aspect, for example, an antibody that is immunologically specific to a peptide having an amino acid sequence that consists of SEQ ID NO 1 is provided. In another aspect, an antibody that is immunologically specific to a peptide having an amino acid sequence that consists of SEQ ID NO 2 is provided. In yet another aspect, an antibody that is immunologically specific to a peptide having an amino acid sequence that consists of SEQ ID NO 3 is provided. In yet another aspect, an antibody that is immunologically specific to a peptide having an amino acid sequence that consists of SEQ ID NO 4 is provided.

The antibodies may be polyclonal, monoclonal, or recombinant, and they may be produced by any method known in the art. Antibody fragments are also considered to be within the scope of the present invention. The antibodies according to aspects of the present invention can be from any animal origin including birds and mammals. In one aspect, for example, antibodies may be derived from human, murine (e.g., mouse and rat), donkey, sheep, rabbit, goat, guinea pig, camel, horse, chicken, etc.

In one aspect, polyclonal antibodies may be utilized to detect and quantify one or more biomarkers described herein in a biological sample to evaluate the risk of preterm birth. Polyclonal antibodies can be produced by various procedures that are well known to those of ordinary skill in the art. For example, polyclonal antibodies may be produced in an in vivo host animal such as a rabbit, a rat, a mouse, a sheep, a goat, etc. The host animal is immunized with either free or carrier-coupled peptides, for example, by intraperitoneal and/or intradermal injection. Injection material is typically an emulsion containing about 100 µg of peptide or carrier protein. Depending on the host species, various adjuvants may be used to increase the immunological response. Examples of adjuvants may include, without limitation, Freund's adjuvant (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as bacille Calmette-Guerin (BCG) and *corynebacterium parvum*. These and other adjuvants are well known in the art. Several booster injections may be required, in some cases at intervals of about two weeks, to provide a useful titer of antibody which can be detected. The titer of antibodies in serum from an immunized animal can be increased by selection of antibodies, e.g., by adsorption of the peptide onto a solid support and elution of the selected antibodies according to methods well known in the art.

In another aspect, monoclonal antibodies may be utilized to detect and quantify one or more biomarkers in a biological sample to evaluate the risk of preterm birth. A monoclonal antibody refers to an antibody that recognizes only one species of antigen. These antibodies are generated by daughter cells of a single antibody-producing hybridoma. A monoclonal antibody typically displays a single binding affinity for any epitope with which it immunoreacts. A monoclonal antibody may contain an antibody molecule having a plurality of antibody combining sites, each immunospecific for a different epitope, e.g., a bispecific monoclonal antibody. Monoclonal antibodies may be obtained by a variety of methods known to those skilled in the art. See, for example, Kohler and Milstein, Nature 256:495 497 (1975); U.S. Pat.

No. 4,376,110; Ausubel et al., eds., Current Protocols in Molecular Biology, Greene Publishing Assoc. and Wiley Interscience, N.Y., (1987, 1992); and Harlow and Lane ANTIBODIES: A Laboratory Manual Cold Spring Harbor Laboratory (1988); Colligan et al., eds., Current Protocols in Immunology, Greene Publishing Assoc. and Wiley Interscience, N.Y., (1992, 1993), each of which are incorporated herein by reference.

It should also be noted that the antibodies useful herein can be monospecific or multispecific (e.g., bispecific, trispecific, or of greater multispecificity). Multispecific antibodies can be specific for different epitopes of a peptide, or they can be specific for both a peptide of interest, and a heterologous epitope, such as a heterologous peptide or solid support material. Moreover, antibodies can also be prepared from any region of the biomarkers described herein.

As an example, monoclonal antibodies can be prepared using well-established methods. In one aspect, monoclonal antibodies are prepared using hybridoma technology. In such a method, a mouse, hamster, or other appropriate host animal, is immunized with an immunizing agent (e.g., a peptide according to aspects of the present invention) to elicit lymphocytes that produce or are capable of producing antibodies that will specifically bind to the immunizing agent. Alternatively, the lymphocytes may be immunized in vitro. The lymphocytes are then fused with an immortalized cell line using a suitable fusing agent, such as polyethylene glycol, to form a hybridoma cell. Immortalized cell lines are often transformed mammalian cells, particularly myeloma cells of rodent, rabbit, bovine and human origin. Often rat or mouse myeloma cell lines are employed. The hybridoma cells may be cultured in a suitable culture medium that may contain one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium") to inhibit growth of HGPRT-deficient cells.

The culture medium in which the hybridoma cells are cultured can be assayed for the presence of monoclonal antibodies. Preferably, the binding specificity of monoclonal antibodies produced by the hybridoma cells is determined by immunoprecipitation or by an in vitro binding assay, such as radioimmunoassay (RIA) or enzyme-linked immunoabsorbent assay (ELISA). Such techniques and assays are known in the art. After hybridoma cells producing desired monoclonal antibodies are identified, the cells may be subcloned by limiting dilution procedures and grown by known methods. The monoclonal antibodies may be isolated or purified from the culture medium by conventional immunoglobulin purification procedures such as, for example, protein A-Sepharose, hydroxylapatite chromatography, gel electrophoresis, dialysis, affinity chromatography, etc. Monoclonal antibodies can also be made by recombinant DNA methods, such as those described in U.S. Pat. No. 4,816,567, which is hereby incorporated by reference. Other methods for generating antibodies known to those of skill in the art are considered to be within the scope of the present invention.

Accordingly, in one aspect a method for testing a pregnant subject for a potential preterm birth is provided. Such a method may include obtaining a biological sample from the subject, contacting the biological sample with an at least one antibody under conditions that allow formation of antibody-antigen complexes, the at least one antibody being immunologically specific to at least one peptide having an amino acid sequence that is identical or homologous to one of the biomarkers described herein, and assaying for formation of the antibody-antigen complexes to detect and quantify the at least one biomarker in the biological sample. The presence and amount of the biomarker of interest in the biological sample would provide an indication of the risk of preterm birth.

As has been described, a variety of immunoassays are known that are capable of detecting and/or quantifying a peptide in a biological sample. In one aspect, the immunoassay may be a competitive assay. For example, a labeled peptide having the sequence of the peptide being tested for is contacted with an antibody specific for at least a portion of the peptide sequence to allow the formation of an antibody-antigen (or peptide) complex. A biological sample is added to the peptide/antibody mixture to allow any peptide of interest present in the biological sample to compete with the labeled peptide, resulting in a decrease in the strength of the label. Competitive assays may include one-step or two-step protocols, which are well known in the art.

In another aspect, the immunoassay may be a noncompetitive, or sandwich assay. Such assays generally provide higher levels of assay sensitivity and specificity. Noncompetitive assay formats may also utilize one- or two-step protocols. Generally such an assay includes antibodies immobilized on a physical support, where the immobilized antibodies are immunologically specific to the peptide (i.e., biomarker) of interest. The biological sample is added to the support along with labeled antibody that is also immunologically specific to the peptide of interest. Peptide present in the biological sample will bind to the immobilized antibody along the support. Labeled antibody also binds to the peptide of interest, and thus is also immobilized to the physical substrate via the peptide and the immobilized antibody. The label on the labeled antibody can then be detected to quantify the amount of biomarker in the biological sample and compared to a control (i.e., a pregnant subject that does not experience preterm birth). In some protocols, non-immobilized labeled antibody can be washed away prior to detection of the label. In this case, the strength of the label is proportional to the amount to amount of biomarker present in the biological sample.

Numerous configurations of solid support substrates are contemplated that are well known in the art. Such a substrate can include any suitable substrate for immobilization of a detection material, such as an antibody or an antibody anchor. For example, a suitable substrate may include any solid support, such as any solid organic, biopolymer, or inorganic support material that is capable of forming bonds with the detection material without significantly affecting the functionality of the antibody. Examples of organic solid support materials may include, without limitation, polymers such as polystyrene, nylon, phenol-formaldehyde resins, acrylic copolymers such as polyacrylamide, etc. Examples of biopolymer support materials may include, without limitation, cellulose, polydextrans, agarose, collagen, chitin, etc. Examples of inorganic support materials may include, without limitations, glass beads (porous and nonporous), stainless steel, metal oxides including porous ceramics such as $ZrO_2$, $TiO_2$, $Al_2O_3$, and NiO, sand, etc.

Numerous specific assay methods known in the art can be sued herein. Such specific assay methods may include protocols such as radioimmunoassays (RIA), enzyme immunoassays (EIA), enzyme linked immunosorbent assays (ELISA), fluorescence immunoassays (FIA), fluorescence polarization immunoassays (FPIA), nephelometric inhibition immunoassays (NIA), microparticle enzyme immunoassays (MEIA), chemiluminescent magnetic immunoassays (CMIA), etc.

Various detectable labels may be coupled to the antibodies according to aspects of the present invention. Appropriate labels may include, without limitation, radionuclides (e.g., $^{125}I$, $^{131}I$, $^{35}S$, $^{3}H$, $^{32}P$, etc.), enzymes (e.g., alkaline phosphatase, horseradish peroxidase, luciferase, beta-glactosidase, etc.), fluorescent moieties or proteins (e.g., fluorescein, rhodamine, phycoerythrin, GFP, BFP, etc.), or luminescent moieties (e.g., Qdot® nanoparticles supplied by the QUANTUM DOT CORP., Palo Alto, Calif.). General techniques to be used in performing the various immunoassays noted above are known to those of ordinary skill in the art.

In addition to immunoassays, additional methods for detection of peptides in the biological sample are contemplated, all of which would be considered to be within the scope of the present invention. In one aspect, for example, mass spectrometry (MS) techniques may be utilized. One specific example may include a high throughput MS analysis technique such as matrix assisted laser desorption ionization. In such a technique, samples may be sent to a specialized facility that can rapidly process hundreds of biological samples per hour.

Also described herein are kits for testing a biological sample from a pregnant subject to evaluate the risk of preterm birth. Such kits may be employed by hospitals, clinics, reference laboratories, doctor's offices, etc. to help make medical decisions and, if necessary, provide available therapies or interventions. Additionally, such kits may also allow the diagnosis, prognosis, or risk assessment of other medical conditions associated with preterm birth.

Accordingly, in one aspect a kit for testing a pregnant subject for potential preterm birth is provided. Such a kit may include at least one monoclonal antibody capable of selectively binding to at least one biomarker having an amino acid sequence SEQ ID NO 1, SEQ ID NO 2, SEQ ID NO 3, and SEQ ID NO 4, and an indicator functionally associated with the antibody to assay formation of an antibody-antigen complex between the at least one monoclonal antibody and the at least one biomarker that can be used to quantify the concentration of the at least one biomarker. The kit may further include any reagents necessary or beneficial for the particular testing assay being utilized.

The kit may contain any means of detecting and quantifying biomarkers in the biological sample, and the contents of the kit may necessarily vary depending on the type of detection assay being used. In addition to necessary reagents, the kit can include antibodies for binding peptides of interest, or fragments thereof, solid substrates, additional antibodies for detection of antibody-antigen complexes, etc. As has been suggested, antibodies or antibody fragments may be present in free form or immobilized to a substrate such as a plastic dish, a test tube, a test rod, beads, etc. The kit can also include suitable reagents for the detection of and/or for the labeling of positive or negative controls, wash solutions, dilution buffers and the like, as well as instructions.

EXAMPLES

The following examples are put forth so as to provide those of ordinary skill in the art with a complete disclosure and description of how the compounds, compositions, and methods described and claimed herein are made and evaluated, and are intended to be purely exemplary and are not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature, and pressure is at or near atmospheric. There are numerous variations and combinations of reaction conditions, e.g., component concentrations, desired solvents, solvent mixtures, temperatures, pressures and other reaction ranges and conditions that can be used to optimize the product purity and yield obtained from the described process. Only reasonable and routine experimentation will be required to optimize such process conditions.

Serum Collection

Studies involved 160 pregnant women having blood withdrawn at 24 or 28 weeks of pregnancy who were followed through the completion of their pregnancy. Eighty of these women had uncomplicated pregnancies with no evidence of preterm birth (PTB). These constituted the control group. Eighty of these women had a PTB (<37 week gestation). These women constituted cases of PTB. The sera of these 160 women were studied using the proteomics techniques described herein.

Acetonitrile Precipitation

Two volumes of HPLC grade acetonitrile (400 µL) were added to 200 µL of serum, vortexed vigorously for 5 sec and allowed to stand at room temperature for 30 min Samples from (Serum collection) were then centrifuged for 10 min at 12,000 rpm in and IEC Micromax RF centrifuge (Thermo Fisher Scientific, Waltham, Mass.) at room temperature. An aliquot of supernatant was then transferred to a microcentrifuge tube containing 300 µL HPLC grade water. The sample was vortexed briefly to mix the solution, which was then lyophilized to ~200 µL in a Labconco CentriVap Concentrator (Labconco Corporation, Kansas City, Mo.). The volume of water added prior to lyophilization aids in the complete removal of acetonitrile from the solution. This is necessary because acetonitrile is incompatible with the assay used to determine protein concentration. Supernatant protein concentration were determined using a Bio-Rad microtiter plate protein assay performed according to manufacturer's instructions. An aliquot containing 4 µg of protein was transferred to a new microcentrifuge tube and lyophilized to near dryness. Samples were brought up to 20 µL with HPLC water and then acidified using 20 µL 88% formic acid.

Acetonitrile treated (post precipitation) serum samples (40 µL) were loaded into 250 µL conical polypropylene vials closed with polypropylene snap caps having septa (Dionex Corporation, Sunnyvale, Calif.), and placed into a FAMOS® autosampler 48 well plate kept at 4° C. The FAMOS® autosampler injected 50 µL of each serum sample onto a liquid chromatography guard column using HPLC water acidified with 0.1% formic acid at a flow rate of 40 µL/min Salts and other impurities were washed off of the guard column with the acidified water. Because the FAMOS® autosampler draws up three times the volume of what is loaded onto the column, it was necessary to inject the samples by hand when sample volume was limited. This was accomplished by injecting 10 µL volume sample onto a blank loop upstream of the guard column and programming the FAMOS® autosampler to inject a 10 µL sample of HPLC water in place of the sample. The serum sample was loaded onto the guard column an desalted as if it had been loaded from the conical vials.

Liquid Chromatography Separation for Mass Spec Analysis

Capillary liquid chromatography (cCL) was performed to fractionate the sample. Capillary LC uses a 1 mm (16.2 µL) microbore guard column (Upchurch Scientific, Oak Harbor, Wash.) and a 15 cm×250 µm i.d. capillary column assembled in-house. The guard column was dry-packed and the capillary column was slurry packed using POROS R1 reversed-phase media (Applied Biosystems, Framingham, Mass.). Column equilibration and chromatographic separation were performed using an aqueous phase (98% HPLC grade $H_2O$, 2% acetonitrile, 01. % formic acid) and an organic phase (2% HPLC $H_2O$, 98% acetonitrile, 0.1% formic acid). Separation was accomplished beginning with a 3 min column equilibration at 95% aqueous solution, followed by a 2.75%/min gradient increase to 60% organic phase, which was then increased at 7%/min to a concentration of 95% organic phase. The gradient was held at 95% organic phase for 7 min to elute the more hydrophobic components of the sample, and then the gradient was returned to 95% aqueous phase over 5 min and held at this concentration for 2 min to re-equilibrate the column. All separations were performed at a flow rate of 5 µL/min Chromatography used an LC Packings Ultimate Capillary HPLC pump system, with FAMOS® autosampler (Dionex Corporation, Sunnyvale, Calif.), controlled by the Analyst QS® (Applied Biosystems, Foster City, Calif.).

MS Analysis

MS calibrations were performed using an external control daily prior to running samples. If needed, settings were adjusted to optimize signal to noise ratio and to maximize sensitivity.

The cLC system was coupled directly to a mass spectrometer. Effluent from the capillary column was directed into a QSTAR Pulsar I quadrupole orthogonal time-of-flight mass spectrometer through an IonSpray source (Applied Biosystems). Data was collected for m/z 500 to 2500 beginning at 5 min and ending at 55 min The delay in start time was programmed because, with a flow rate of 5 µL/min, it takes over 5 min for sample to get from the guard column to the mass spectrometer, and thus no useful data can be obtained before 5 min Data collection, processing and preliminary formatting are accomplished using the Analyst QS® software package with BioAnalyst add-ons (Applied Biosystems).

Mass spectra were obtained every 1 sec throughout the entire cLC elution period for each specimen from 5 minutes to 55 minutes. The elution profile of the cLC fractionated protein depleted serum of each subject, reported as the total ion chromatogram, was inspected to insure that it was consistent with previously run human sera. Specimens having an overall abundance less than 50% of normal or greater than 200% normal or lacking the characteristic series of three broad ion intense regions were rerun or omitted if there was inadequate specimen to redo the analysis.

Peak Alignment

Because samples run on different days and columns can vary in elution time, 10 endogenous molecular species of average abundance that elute at approximately 2 minute intervals throughout the useful chromatogram (useful chromatogram approximately 15 minutes to 35 minutes) were determined. Two-minute windows were established over the elution region of interest to allow file size to remain manageable. The Extract Ion Chromatogram (XIC) function of the MS computer is used to visualize the elution of the desired m/z ranges for each elution time marker. Each of the alignment peaks elution time is then determined for each specimen run and in turn used as the center of a 2 min window by means of the Set Selection function. This aligns all runs to the same midpoint for that window. Then the Show Spectra function can be used to create a single averaged mass spectrum from all the mass spectra.

Data Analysis

Analyst®, the software program supporting the Q-Star (q-TOF) mass spectrometer, allows for compilation of 16 individual liquid chromatographic runs and the comparison of mass spectra within those runs at similar elution times. Ten two-minute windows were established as described above over the 20 minute period of useful elution to allow data file size to remain manageable. The two minute windows were aligned as is also described above. Of the 10 two minute elution intervals, the first to be analyzed was the second two-minute window, chosen because there were typically more peptide species present. Peptides were identified by the characteristic appearance of their multiply charged states, which appear as a well defined cluster of peaks having a Gaussian shape with the individual peaks being separated by less than 1 mass/charge unit rather than a single peak or peaks separated by 1 mass/charge unit. Groups of 8 subjects experiencing PTB and 8 subjects from controls (no PTB) were color coded and overlaid. The data was then visually inspected and molecular species that seemed to be dominated by one color were recorded. The software used was limited to visualizing only 16 samples. For a sampling size larger than 16, multiple comparisons of data sets were made. For a compound to be considered further, the same apparent difference between the two groups was needed to be observed in at least two thirds of the data sets.

Molecules that appeared to be different between the two study groups were then individually inspected. These candidate species were all peptides. Prior to extracting quantitative data, the mass spectrum was examined to insure that the peptide peak had the same m/z and also represented the same charge state to further insure that the same peptide was being considered. Additionally, a second nearby peak, which did not demonstrate differences in abundance between the two groups, was selected as a reference. This peak was used to normalize the candidate peak of interest and correct for variability in specimen processing, specimen loading and ionization efficiencies.

The molecular species are then 'extracted' by the Analyst® software to determine the peak maxima of the individual molecular species in each individual run. This feature did not limit inspection of a specific m/z to a two minute elution window and consequently the peak used to align cLC elution time may be used additionally to insure the location in the elution profile was the same and hence insure that the same molecular species was selected each time.

The peak height for each molecular species was considered a reasonable estimate of its abundance. The abundance of each candidate compound was tabulated and the calculated value of each candidate species was ratioed to the nearby reference species. Because a single species was being considered, univariate statistical analysis was employed in evaluating possible differences in this peptide's abundance between the two groups.

Endogenous Time Alignment Molecules

The mass and typical elution time of the reference peaks used for time alignment are summarized in Table 1.

TABLE 1

Mass and Elution Time of the Time Alignment Markers

| Mass of Endogenous Time Reference (daltons) | Mean Elution Time (min) |
|---|---|
| 1464.65 | 14.68 |
| 1439.52 | 17.01 |
| 2009.95 | 18.83 |
| 5062.28 | 21.34 |
| 546.31 | 23.54 |
| 545.33 | 26.12 |
| 1046.67 | 27.60 |
| 636.31 | 32.44 |
| 779.52 | 34.59 |
| 1619.07 | 36.88 |

Knowledge of the location of these endogenous molecular species present in all sera of pregnant women also allows them to be used for time markers for the alignment and localization of the PTB biomarkers within capillary liquid chromatography elution profile.

Biomarker Characteristics

After time alignment, biomarker candidates were identified visually in an initial process where multiple mass spectra were overlaid with PTB cases and controls each assigned a color. Those peaks that appear to be predominantly one color were studied further. The individual spectra were then submitted to peak height determination by the computer equipped with Analyst® software (Applied Biosystems) which is the operating system for the QqTOF mass spectrometer (Applied Biosystems). The quantity of the biomarkers was then tabulated. In addition, a second peak that occurred in the same time window, which was not quantitatively different between cases and controls, was also selected. This represented a endogenous control to allow for reduction of non-biologic variability. This was accomplished by dividing the quantity of the candidate peak by the quantity of the endogenous control. The magnitude of the ratio for each specimen was recorded and statistical differences were sought using a Student's t test comparing PTB cases and controls.

Four species were sufficiently different ($p \leq 0.0001$) to suggest that they might allow for excellent separation of the two groups. The individual masses and elution time for the four PTB biomarkers are summarized in Table 2.

TABLE 2

Mass and Elution Time of the Biomarkers

| | Peak (m/z) | Mean Mass | Mean Elution Time |
|---|---|---|---|
| 1. | 676.7 | 2026.98 | 14.30 ± 0.47 |
| 2. | 856.8 | 4279.25 | 17.20 ± 2.04 |
| 3. | 860.0 | 4295.25 | 16.13 ± 1.97 |
| 4. | 794.8 | 3968.96 | 15.52 ± 0.15 |

The elution time (retention time) was expressed as a function of the internal time controls. This was determined by the relative position of the peak of interest between the time marker that precedes the biomarker and the time marker that followed the peak of interest. This was calculated by the following formula:

$R_f$=(elution time of biomarker−elution time of preceding time marker)/(elution time of following time marker−elution time of preceding time marker)

The $R_f$ values were more reliable than the actual elution times. Elution times may vary with new columns or with the altered performance of an existing column with fouling, but the $R_f$ was not altered by these changes. The $R_f$ values of the five biomarkers are provided in Table 3.

TABLE 3

The $R_f$ Values for the PTB Biomarkers Using the Internal Time Alignment Peaks.

| | Peak (m/z) | N | $R_f$ Value Relative To Boundary Time Markers |
|---|---|---|---|
| 1. | 676.7 | 12 | 0.535 ± 0.052 (between time markers 2 and 3) |
| 2. | 856.8 | 12 | 0.781 ± 0.086 (between time markers 2 and 3) |
| 3. | 860.0 | 9 | 0.695 ± 0.134 (between time markers 2 and 3) |
| 4. | 794.8 | 10 | 0.0252 ± 0.021 (between time markers 3 and 4) |

Reduction of Variability by Reference to an Endogenous Coeluting Control

One of the features of the current serum proteomic approach is the use of an endogenous molecule that was found in all species and was not different between cases and controls. Normalization of biomarker abundance to this internal control reduced non-biological variation and improved the ability to utilize biomarkers in risk prediction. Normalization involved mathematically dividing the abundance of the peak of interest by the reference peak. The abundances were machine derived values. The abundance of a given molecule represents the number of ions of a particular mass measured by the mass spectrometer in a given mass spectrum or the sum of the number ions of a specific mass observed in several mass spectra representing the full elution interval. Molecules typically require 1.0-1.5 min to move off the chromatographic column whereas mass spectra are acquired every 1 second during that elution interval.

For the current four peaks internal references were used. For the biomarker peak m/z 676.7, a coeluting reference peak at m/z 673.3 was used. For the biomarker m/z 856.8 and 860.0, a coeluting reference peak at m/z 843.8 was chosen. For the biomarker m/z 794.8, a coeluting reference at m/z 595.3 was chosen. Using these ratios the mean value for the log ratios were calculated (Table 4):

TABLE 4

Biomarker Abundance (after Normalization) in Cases and Controls

| | Ratio | Mean Control | Mean PTB | P value |
|---|---|---|---|---|
| 1. | log 676.7/673.3 | 0.579 ± 0.101 | −0.015 ± 0.090 | 2 × 10$^{-6}$ |
| 2. | log 856.8/842.8 | 0.231 ± 0.102 | −0.149 ± 0.095 | 0.0004 |
| 3. | log 860.0/842.8 | 0.201 ± 0.096 | −0.204 ± 0.088 | 0.001 |
| 4. | log 794.8/595.3 | 0.582 ± 0.637 | 0.274 ± 0.656 | 0.018 |

Use of the Biomarkers to Predict Women at Risk of Experiencing Preterm Birth

As described above, one common measure of the predictive power of a biomarker was its sensitivity and specificity. A threshold for each of the four log ratios in Table 4 was determined in order to identify subjects at risk of developing PTB. The threshold for each was calculated such that there would be a specificity (a true negative rate) of 80% or more. As stated, this is the same as a false positive rate of no more than 20%. Using these mathematically determined thresholds the four ratios independently provided the following sensitivity (true positive) and specificity (true negative) rates as summarized in Table 5.

TABLE 5

Sensitivity and Specificity of Each Biomarker (after Normalization)

| | Ratio | Threshold | Sensitivity | Specificity |
|---|---|---|---|---|
| 1. | log 677/673 | <0.00 | 65% | 85% |
| 2. | log 857/843 | <−0.347 | 38% | 82% |

TABLE 5-continued

Sensitivity and Specificity of Each Biomarker (after Normalization)

| | Ratio | Threshold | Sensitivity | Specificity |
|---|---|---|---|---|
| 3. | log 860/843 | <−0.222 | 55% | 80% |
| 4. | log 795/595 | <0.151 | 45% | 82% |

Sensitivity is a statistical term defined as the true positive rate or specifically in this case the percentage of pregnant women who later develop PTB that are correctly identified by the biomarker. The specificity is defined as the true negative rate or in this case the percentage of pregnant women with uncomplicated pregnancies correctly identified. To use a biomarker for prediction in this manner a numeric threshold must be established. To establish that numeric value, typically the range of values for the biomarker are considered from lowest to highest and at each point the percent of subjects correctly identified as positive and at that same point the percent of controls incorrectly identified as positive. This is termed a receiver operator curve (ROC). The false positive rate is limited to 20%. This is commonly considered the maximum tolerated for a clinical test. The false positive rate (the percentage of women with uncomplicated pregnancies, the control group, identified by the biomarker as at risk for later PTB) is calculated from the true negative rate being subtracted from 100%. Whatever the threshold is at a false positive rate of 20% or less (which is equivalent to a specificity of 80% or higher) determines the threshold used to determine whether someone is at risk or is not at risk. A threshold for each of the four ratios was determined that allowed for the identification of subjects at risk of later PTB. The threshold for each was calculated such that there would be a specificity (a true negative rate) of 80% or more. As stated this is the same as a false positive rate no more than 20%. Using these mathematically determined thresholds the four ratios independently provided the following sensitivity (true positive) and specificity (true negative) rates as summarized in Table 5. Combinations of peaks did not significantly improve on the ability of the peak at 677 to predict later PTB.

Identity of Current PTB Biomarkers

Using tandem MS with a collision cell in between the two mass spectrometers to cause fragmentation of the parent peptide, the amino sequences were determined from the fragmentation pattern observed in the second MS step with comparison to searchable database (MASCOT). Three of the peptides were derived from the same parent protein, inter-alpha trypsin inhibitor, heavy chain 4 (ITIH4), whereas the final peptide was obtained from a second protein, inter-alpha trypsin inhibitor heavy chain related protein (IHRP). Table 6 provides of the biomarkers (SEQ ID NOS 1-4, respectively).

TABLE 6

Amino acid sequences for the 4 biomarker peptides

| M/z | MW | Sequence | Parent Protein |
|---|---|---|---|
| 677 | 2026.98 | qlglpgppdvpdhaayhpf | ITIH4-2 |
| 857 | 4279.25 | nvhsagaagsrmnfrpgvlssrqlglpgppdvpdhaayhpf | ITIH4-2 |
| 860 | 4295.25 | nvhsagaagsrm(O)nfrpgvlssrqlglpgppdvpdhaayhpf | ITIH4-2 |
| 795 | 3969.96 | nvhsgstffkyylqgakipkpeasfspr | IHR4-1 |

These peptides appear to arise from a protein super family termed the inter-alpha trypsin inhibitors. More specifically, the peptides appear to be derived from two different proteins that are currently considered isoforms of inter-alpha trypsin inhibitor heavy chain 4, isoform 1 (ITIH4-1) and isoform 2 (ITIH4-2). The two isoforms have some sequence homology but also have sections of amino acids that are not found in the other. The two isoforms do not simply represent a truncation one of the other.

ELISA Assay I

The following ELISA assay can be utilized to detect and quantify a biomarker of interest in a biological sample. A first antibody immunologically specific to the peptide of interest (antigen) is adsorbed onto the surface of a 96 well microtiter plate. 25 microliters of serum or standard of known, graded concentration of the peptide of interest is added to individual wells. The serum is incubated with the first antibody for 30 min. The first antibody coated on the well surface binds the antigen, immobilizing it. 200 micoliters of a second solution containing a second antibody that is also immunologically specific to the antigen is added to each well. The second antibody has been labeled with a marker such as horseradish peroxidase or a chemiluminescent precursor. The wells are incubated for 30 minutes to allow binding of the second antibody to the antigen-first antibody complex to form an antibody-antigen-antibody 'sandwich' which is itself bound to the well surface. The well is then carefully and fully washed to remove any unbound second antibody. Then, a solution containing a specific substrate to the second antibody label is added. In the case of horseradish peroxidase, a color change occurs in the well corresponding to the amount of bound second antibody. In the case of the chemiluminescent marker, the substrate is converted from a non-chemiluminescing molecular species into a chemiluminescent product that glows. The light emitted by the product is proportional to the amount of antigen present in the well and is measured by a 'plate reader,' a specialized spectrometer that measures the light emitted at a specific wavelength and records its intensity.

ELISA Assay II

The following ELISA assay can be utilized to detect and quantify a biomarker of interest in a biological sample. This assay is similar to the ELISA Assay I, with the exception that the second antibody is labeled with a biotin molecule. Following washing of the wells following antibody-antigen-antibody formation, a solution containing streptavidin bound to horseradish peroxidase is added to the wells to allow reaction with the biotin molecule. In this particular assay an uncolored substrate is converted to a colored product. The intensity of the color, measured as its absorbance of light of a particular wavelength, is proportional to the amount of antigen present in the well. The concentration of an unknown can be estimated by comparison of its absorbance to a plot of absorbance versus concentration of series of calibrating standards of known, graded concentrations of antigen.

It is to be understood that the above-described compositions and modes of application are only illustrative of preferred embodiments of the present invention. Numerous modifications and alternative arrangements may be devised by those skilled in the art without departing from the spirit and scope of the present invention and the appended claims are intended to cover such modifications and arrangements. Thus, while the present invention has been described above with particularity and detail in connection with what is presently deemed to be the most practical and preferred embodiments of the invention, it will be apparent to those of ordinary skill in the art that numerous modifications, including, but not limited to, variations in size, materials, shape, form, function and manner of operation, assembly and use may be made without departing from the principles and concepts set forth herein.

What is claimed:

1. A method of identifying subjects at risk for preterm birth, the method comprising the steps of:
   (a) protein depleting a serum or blood sample from a pregnant subject, wherein the protein depleting includes treating the serum or blood sample with a volume of acetonitrile;
   (b) fractionating the protein depleted sample to isolate at least one biomarker selected from the group consisting of SEQ ID NO: 1, SEQ ID NO: 2, and SEQ ID NO: 3;
   (c) detecting a concentration of the at least one isolated biomarker by mass spectrometry; and
   (d) identifying the pregnant subject as being at risk for preterm birth when the concentration of the at least one isolated biomarker is less than a control concentration of the at least one biomarker.

2. The method of claim 1, wherein the serum or blood sample is obtained from the pregnant subject at about 20 to about 34 weeks gestation.

3. The method of claim 1, wherein the serum or blood sample is obtained from the pregnant subject at about 22 to about 28 weeks gestation.

4. The method of claim 1, wherein the identifying includes identifying the pregnant subject as being at risk for preterm birth when the concentration of SEQ ID NO: 1 or SEQ ID NO: 2 is about 50% or less of the control concentration of SEQ ID NO: 1 or SEQ ID NO: 2 and the serum or blood sample is obtained when the pregnant subject is at least 22 weeks gestation.

5. The method of claim 1, wherein the identifying includes identifying the pregnant subject as being at risk for preterm birth when the concentration of SEQ ID NO: 3 is about 55% or less of the control concentration of SEQ ID NO: 3 and the serum or blood sample is obtained when the pregnant subject is at least 22 weeks gestation.

6. The method of claim 1, wherein the detecting further includes detecting the control concentration of the at least one biomarker present in a control biological sample.

7. The method of claim 1, wherein the identifying includes identifying the pregnant subject as being at risk for preterm birth when the concentration of SEQ ID NO: 1 or SEQ ID NO: 2 is about 30% or less than the control concentration of SEQ ID NO: 1 or SEQ ID NO: 2 and the serum or blood sample is obtained when the pregnant subject is at least 22 weeks gestation.

8. The method of claim 1, wherein the identifying includes identifying the pregnant subject as being at risk for preterm birth when the concentration of SEQ ID NO: 3 is about 35% or less of the control concentration of SEQ ID NO: 3 and the serum or blood sample is obtained when the pregnant subject is at least 22 weeks gestation.

9. The method of claim 1, wherein the identifying includes identifying the pregnant subject as being at risk for preterm birth when the concentration of SEQ ID NO: 1 or SEQ ID NO: 2 is about 10% or less than the control concentration of SEQ ID NO: 1 or SEQ ID NO: 2 and the serum or blood sample is obtained when the pregnant subject is at least 22 weeks gestation.

10. The method of claim 1, wherein the identifying includes identifying the pregnant subject as being at risk for preterm birth when the concentration of SEQ ID NO: 3 is about 15% or less of the control concentration of SEQ ID NO: 3 and the serum or blood sample is obtained when the pregnant subject is at least 22 weeks gestation.

11. The method of claim 1, wherein the fractionating includes fractionating the protein depleted sample by capillary liquid chromatography to isolate the at least one biomarker.

12. A method of identifying subjects at risk for preterm birth, the method comprising the steps of:
   (a) protein depleting a serum or blood sample from a pregnant subject, wherein the protein depleting includes treating the serum or blood sample with a volume of acetonitrile;
   (b) fractionating the protein depleted sample to isolate an endogenous reference molecule and at least one biomarker selected from the group consisting of SEQ ID NO: 1, SEQ ID NO: 2, and SEQ ID NO:3;
   (c) obtaining a mass ion peak corresponding to the at least one biomarker and a mass ion peak corresponding to the endogenous reference: molecule;
   (d) measuring abundances of the at least one biomarker and the endogenous reference molecule from the mass ion peaks; and
   (e) identifying the pregnant subject as being at risk for preterm birth when the abundance of the at least one biomarker is less than the abundance of the endogenous reference molecule.

13. The method of claim 12, wherein the mass ion peak corresponding to SEQ ID NO: 1 is 677 and the mass ion peak corresponding to the endogenous reference molecule is 673.

14. The method of claim 12, wherein the mass ion peak corresponding to SEQ ID NO: 2 is 857, the mass ion peak corresponding to SEQ ID NO: 3 is 860, and the mass ion peak corresponding to the endogenous reference molecule is 843.

15. The method of claim 12, wherein the identifying includes identifying the pregnant subject as being at risk for preterm birth when a ratio of the abundance of SEQ ID NO: 1 to the abundance of the endogenous reference molecule is less than about 0.8 and the serum or blood sample is obtained when the pregnant subject is at least 22 weeks gestation.

16. The method of claim 12, wherein the identifying includes identifying the pregnant subject as being at risk for preterm birth when a ratio of the abundance of SEQ ID NO: 2 or SEQ ID NO: 3 to the abundance of the endogenous reference molecule is less than about 0.6 and the serum or blood sample is obtained when the pregnant subject is at least 22 weeks gestation.

* * * * *

UNITED STATES PATENT AND TRADEMARK OFFICE
CERTIFICATE OF CORRECTION

PATENT NO. : 10,247,736 B2
APPLICATION NO. : 12/669343
DATED : April 2, 2019
INVENTOR(S) : Steven William Graves et al.

It is certified that error appears in the above-identified patent and that said Letters Patent is hereby corrected as shown below:

In the Specification

Column 1 Line 18 delete the following:
"The research leading to this invention was funded in part by the National Institutes of Health, Grant Nos. R21HD047319 and U01HD050080. The U.S. Government has certain rights in this invention."

And replace it with:
"This invention was made with government support under grant nos. R21 HD047319 and U01 HD050080 awarded by the National Institutes of Health. The government has certain rights in the invention."

Signed and Sealed this
Twenty-eighth Day of January, 2020

Andrei Iancu
*Director of the United States Patent and Trademark Office*